(12) United States Patent
Alqahtani

(10) Patent No.: US 9,311,827 B1
(45) Date of Patent: Apr. 12, 2016

(54) WEARABLE ASSISTIVE DEVICE, SYSTEM AND METHODS THEREOF FOR THE VISUALLY IMPAIRED

(71) Applicant: Amal Abdullah Alqahtani, Pittsburgh, PA (US)

(72) Inventor: Amal Abdullah Alqahtani, Pittsburgh, PA (US)

( * ) Notice: Subject to any disclaimer, the term of this patent is extended or adjusted under 35 U.S.C. 154(b) by 0 days.

(21) Appl. No.: 14/543,137

(22) Filed: Nov. 17, 2014

(51) Int. Cl.
*G09B 21/00* (2006.01)
*G08B 3/00* (2006.01)
*G08B 6/00* (2006.01)

(52) U.S. Cl.
CPC ............ *G09B 21/007* (2013.01); *G08B 3/00* (2013.01); *G08B 6/00* (2013.01)

(58) Field of Classification Search
None
See application file for complete search history.

(56) References Cited

U.S. PATENT DOCUMENTS

| 7,446,669 B2 | 11/2008 | Liebermann |
| 8,531,291 B2 | 9/2013 | Tran |
| 8,630,633 B1 | 1/2014 | Tedesco et al. |
| 2013/0220392 A1* | 8/2013 | Gassert ............ A61H 3/061 135/66 |

FOREIGN PATENT DOCUMENTS

| CN | 202355554 U | 8/2012 |
| JP | 2003093454 A | 4/2003 |
| KR | 10-1193721 B1 | 10/2012 |

OTHER PUBLICATIONS

Ramiro Velázquez, "Wearable Assistive Devices for the Blind", pp. 331-349, 2010, http://www.robotica-up.org/PDF/Wearable4Blind.pdf.

* cited by examiner

*Primary Examiner* — Daniell L Negron
(74) *Attorney, Agent, or Firm* — Oblon, McClelland, Maier & Neustadt, L.L.P.

(57) ABSTRACT

A wearable assistive device or system utilizing touch as a sensory modality to assist the ambulation of the visually impaired. The wearable assistive device or system is worn on a user's leg, and includes a pair of robotic arms that grip the ankles upon the detection of an object by an ultrasonic sensor within a predetermined distance. The device is also GPS-enabled to assist the navigation of a user from one place to another. The wearable assistive device is controlled by a computing device that is worn on the same foot or other foot of the user.

20 Claims, 8 Drawing Sheets

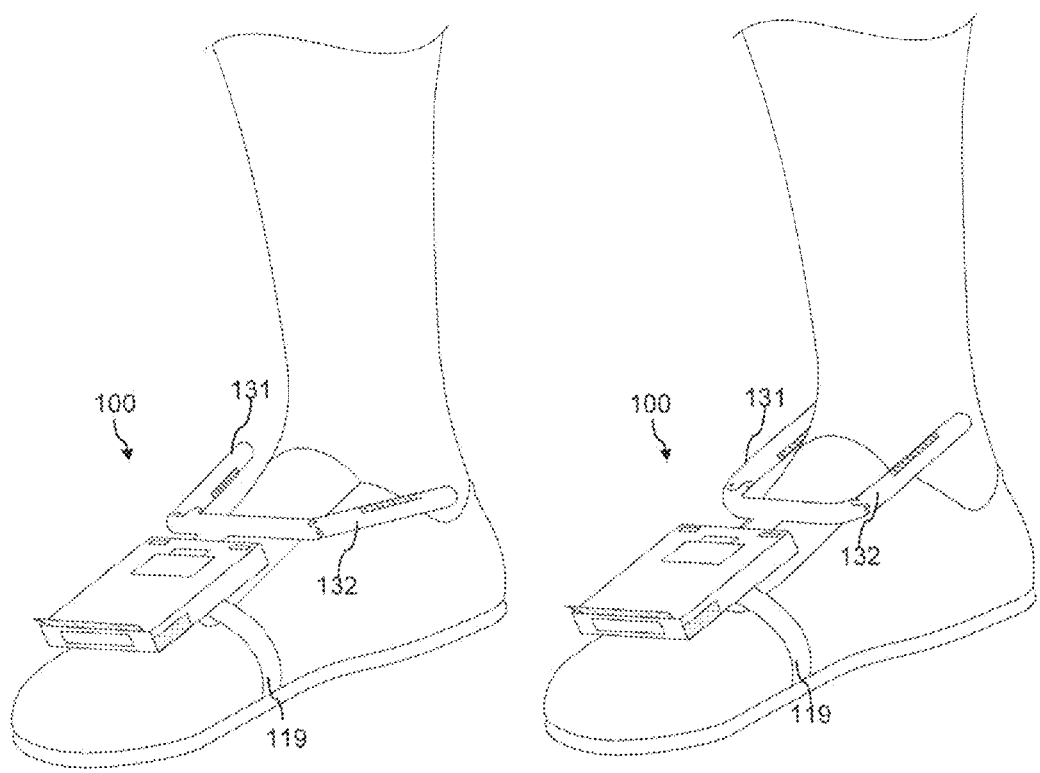

WEARABLE ASSISTIVE DEVICE, SYSTEM AND METHODS THEREOF FOR THE VISUALLY IMPAIRED

GRANT OF NON-EXCLUSIVE RIGHT

This application was prepared with financial support from the Saudi Arabian Cultural Mission, and in consideration therefore the present inventor(s) has granted The Kingdom of Saudi Arabia a non-exclusive right to practice the present invention.

SUMMARY

A non-limiting objective of the present invention is to provide devices, systems and methods for utilizing one or more sensory modalities to emit stimuli or signals that assist the mobility and ambulation of the visually impaired.

According to a broad aspect, the present invention relates to a hands-free, wearable assistive device configured to be worn on a portion of a leg of a user. The wearable assistive device comprises an ultrasonic sensor configured to detect an object within a predetermined distance in front of the device and the user, a processing circuitry configured to determine a plurality of characteristics of the object and identify the object based on detection signals from the ultrasonic sensor, and to determine when the object is within the predetermined distance, a GPS tracker circuitry configured to determine a real-time location of the user and to provide commands to output audible and/or tactile directions to a desired destination, first and second robotic arms configured to grip the portion of the user's leg when the processing circuitry determines the object is within the predetermined distance in front of the device and based on the commands from the GPS tracker circuitry.

In one or more embodiments, the characteristics of the object comprise one or more dimensions, color and orientation of the object.

In one or more embodiments, the wearable assistive device further comprises a motion sensor.

In one or more embodiments, the ultrasonic sensor is further configured to detect motion.

In one or more embodiments, the wearable assistive device further comprises a light emitter.

In one or more embodiments, the wearable assistive device further comprises one or more speakers, each of which is configured to emit auditory signals and/or messages when the ultrasonic sensor detects the object and to emit object-specific auditory signals and/or messages when the processing circuitry determines the characteristics of the object and identifies the object.

In one or more embodiments, the wearable assistive device further comprises first and second vibrators on the first and the second robotic arms, respectively, each of which is configured to emit vibrations when the ultrasonic sensor detects the object and to emit object-specific vibrations when the processing circuitry determines the characteristics of the object and identifies the object.

According to another broad aspect, the present invention relates to a hands-free, wearable assistive system configured to be worn on a portion of one or more legs of a user The wearable assistive system comprises a device including an ultrasonic sensor configured to detect an object within a predetermined distance in front of the device and the user, and to determine the characteristics of the object and to identify the object, a GPS tracker configured to determine a real-time satellite location of a user and to provide audible and/or tactile directions to a desired destination, first and second robotic arms configured to grip the user's ankle when the ultrasonic sensor detects the object within the predetermined distance in front of the device and the user and grip the user's ankle in an object-specific pattern when the ultrasonic sensor identifies the object and a controller electrically connected to the device. The controller includes a processor, a main memory and a database of geometrical shape dimensions mapped to multiple predetermined objects.

In one or more embodiments, the characteristics of the object comprise one or more dimensions, color and orientation of the object.

In one or more embodiments, the controller is a built-in controller inside the device.

In one or more embodiments, the wearable assistive system further comprises a motion sensor.

In one or more embodiments, the ultrasonic sensor is further configured to detect motion.

In one or more embodiments, the wearable assistive system further comprises a Bluetooth or a Wifi transponder that connects the wearable assistive system to a mobile communication device.

In one or more embodiments, the wearable assistive system further comprises a light emitter.

In one or more embodiments, the wearable assistive system further comprises one or more speakers, each of which is configured to emit auditory signals and/or messages when the ultrasonic sensor detects the object and to emit object-specific auditory signals and/or messages when the ultrasonic sensor determines the characteristics of the object and identifies the object.

In one or more embodiments, the wearable assistive system further comprises first and second vibrators on the first and the second robotic arms, respectively, each of which is configured to emit vibrations when the ultrasonic sensor detects the object and to emit object-specific vibrations when the ultrasonic sensor determines the characteristics of the object and identifies the object.

According to yet another broad aspect, the present invention relates to a method of providing mobility assistance to a user. The method comprises providing a hands-free, wearable assistive device or system configured to be worn on one or more ankles of the user, detecting an object using an ultrasonic sensor of the system, determining, using a processor, whether the object is within a predetermined distance, gripping the one or more ankles of the user, when the object is within the predetermined distance, using first and second robotic arms of the system and providing, using a GPS tracker, audible and/or tactile indications of directions to a desired destination.

In one or more embodiments, the method further comprises determining one or more characteristics of the object and identifying the object using the ultrasonic sensor and the processor and gripping the user's ankle in an object-specific pattern based on the determination.

In one or more embodiments, the method further comprises emitting auditory signals and/or messages when the ultrasonic sensor detects the object, using one or more speakers and emitting object-specific auditory messages when the processor determines the one or more characteristics of the object and identifies the object, using the one or more speakers.

In one or more embodiments, the method further comprises emitting vibrations when the ultrasonic sensor detects the object, using first and second vibrators on the robotic arms, respectively and emitting object-specific vibrations when the processor determines the one or more characteristics of the object and identifies the object, using the first and second vibrators on the robotic arms.

The foregoing paragraphs have been provided by way of general introduction, and are not intended to limit the scope of the following claims. The described embodiments will be best understood by reference to the following detailed description taken in conjunction with the accompanying drawings.

BRIEF DESCRIPTION OF THE DRAWINGS

The accompanying drawings, which are incorporated in and constitute a part of the specification, illustrate one or more embodiments and, together with the description, explain these embodiments. The accompanying drawings have not necessarily been drawn to scale. Any values and dimensions illustrated in any accompanying graphs and figures are for illustration purposes only and may or may not represent actual or preferred values or dimensions. Where applicable, some or all features may not be illustrated to assist in the description of the underlying features. In the drawings:

FIG. 2 is a schematic illustration of the wearable assistive device of FIG. 1 worn on a user according to a first configuration.

FIG. 3 is a schematic illustration of the wearable assistive device of FIG. 1 worn on a user according to a second configuration.

DETAILED DESCRIPTION

Figure 1:
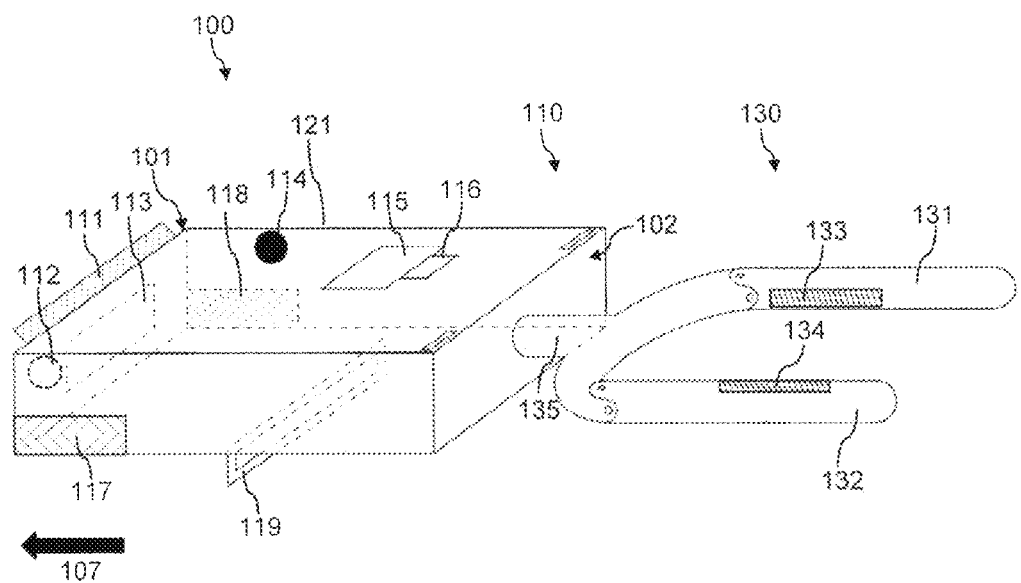
FIG. 1 is a schematic illustration of a portion of a wearable assistive apparatus or device according to one or more embodiments.

The description set forth below in connection with the appended drawings is intended as a description of various embodiments of the invention and is not necessarily intended to represent the only embodiments in which the invention may be practiced. In certain instances, the description includes specific details for the purposes of providing an understanding of the invention. However, it will be apparent to those skilled in the art that the invention may be practiced without these specific details. In some instances, well-known structures and components may be shown in block diagram form in order to avoid obscuring the concepts of the disclosed subject matter.

Reference through the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments. Additionally, it must be noted that, as used in the specification and the appended claims, the singular forms "a," "an," and "the" include plural referents unless the context clearly dictates otherwise. That is, unless clearly specified otherwise, as used herein the words "a" and "an" and the like carry the meaning of "one or more." Further, it is intended that the present invention and embodiments thereof cover the modifications and variations. For example, it is to be understood that terms such as "left," "right," "top," "bottom," "front," "rear," "side," "height," "length," "width," "upper," "lower," "interior," "exterior," "inner," "outer," and the like that may be used herein, merely describe points of reference and do not necessarily limit the present invention to any particular orientation or configuration. Furthermore, terms such as "first," "second," "third," etc., merely identify one of a number of portions, components and/or points of reference as disclosed herein, and likewise do not necessarily limit the present invention to any particular configuration or orientation.

Described herein are devices and systems and methods that can assist the mobility or ambulation of a visually impaired person. A visually impaired person, as used herein, refers to a person who is temporarily or permanently completely blind, or temporarily or permanently with low or reduced vision. In some cases, the visually impaired person may have a condition wherein it is very difficult for him or her to estimate the distance between himself or herself and the object. The object may be stationary or moving.

In wearable technology, wearable devices can allow hands-free interaction for the user, or at least may minimize the use of one or more hands when using the wearable device or when the wearable device is operative. As discussed in more detail below, the wearable assistive device or system according to various embodiments of the present invention can be worn around or otherwise coupled to one or more legs or feet or a user, for example, around or to one or more ankle portions. Providing an assistive device at one or more of a user's legs or feet can be beneficial in detecting objects or obstacles, as a user's foot or leg may be closer to the object or obstacle when the user is walking or running. However, embodiments of the present invention are not so limited, and the wearable assistive device, components thereof, or the system may be fully or partly arranged or coupled to another part of a user's body, such as one or more of the user's wrists or hands (since these portions also lead when walking or running), a user's waist, head or neck.

FIG. 1 provides a view of a wearable assistive device 100 according to an embodiment of the present invention, while FIGS. 2 and 3 illustrate an example of how the device 100 may be worn on a user. According to this embodiment, wearable assistive device 100 can comprise an electronic component 110 that may be attached to a user's shoe and a mechanical component 130 that may be fitted around the user's leg, at the ankle, for instance. The electronic component 110 may be of any geometrical shape and any size. For example, the electronic component may have a width and length of the size of a shoe or a user's foot.

The electronic component 110 can include an ultrasonic sensor 111, optionally a GPS tracker 112, optionally a light emitter 113, a switch 114, an information display screen 115, a time display screen 116, one or more speakers 117, 118 and a fastener 119.

The ultrasonic sensor 111 can detect and identify stationary and moving objects or obstacles when the wearable assistive device 100 is moving forward and/or backward, such as when a user is walking or running, sideways, such as when a user is changing his or her course or direction. In one or more embodiments, the ultrasonic sensor 110 can contain a plurality of sensor devices to sense a user's surroundings. Each of the sensors can be configured to detect and/or identify objects and obstacles that are in front, on the right, on the left, or behind the user.

Mechanical component 130 can include main arm 135 that bifurcates into two robotic or movable arms 131, 132. The mechanical component can also include an actuator or a motor that moves or controls the mechanism of the robotic arms 131, 132. As shown in FIGS. 2 and 3, when worn by a user, robotic arms 131, 132 can wrap around the ankles of the user or extend on opposite side of the leg. In FIG. 2, robotic arms 131, 132 are in an unactivated mode or state. In FIG. 3, the robotic arms are activated so as to tighten and grip the user's ankles which may signify an alert or alarm of an object or obstacle detected and/or identified by the electronic component 110. In certain embodiments, the robotic arms 131, 132 may each include a vibrator 133, 134 on the inside of the arm. The vibrators can emit vibrations that may be felt upon the user's ankles when the robotic arms are activated to grip the ankles, as shown in FIG. 3, and may also signify an alert, an alarm or otherwise indicate the detection of an object or obstacle or indicate a direction of movement the user should take.

In the embodiments shown in FIGS. 1-5, electronic component 110 is of a rectangular shape whose size and shape are defined by casing 121. In one or more embodiments, wearable assistive device 100 can weigh no more than 250 g, no more than 200 g, or between 150-200 g, for instance. Of course, the size, shape and weight are not so limited.

The ultrasonic sensor 111, GPS tracker 112 and light emitter 113 can be mounted on a first side surface 101 which maybe a generally flat surface. The ultrasonic sensor can be an ultrasonic transducer that detects objects that are in front of it within proximity of 2 centimeters to 3 meters by emitting ultrasonic vibrations in a direction indicated by arrow 107 and evaluating attributes of a detected object by interpreting the echoes from radio or sound waves. Attributes that can be evaluated include distance between the detected object and the user, size, shape, dimensions, color and/or orientation of the detected object. In some embodiments, the ultrasonic sensor can also function as a motion detector.

Figure 4:
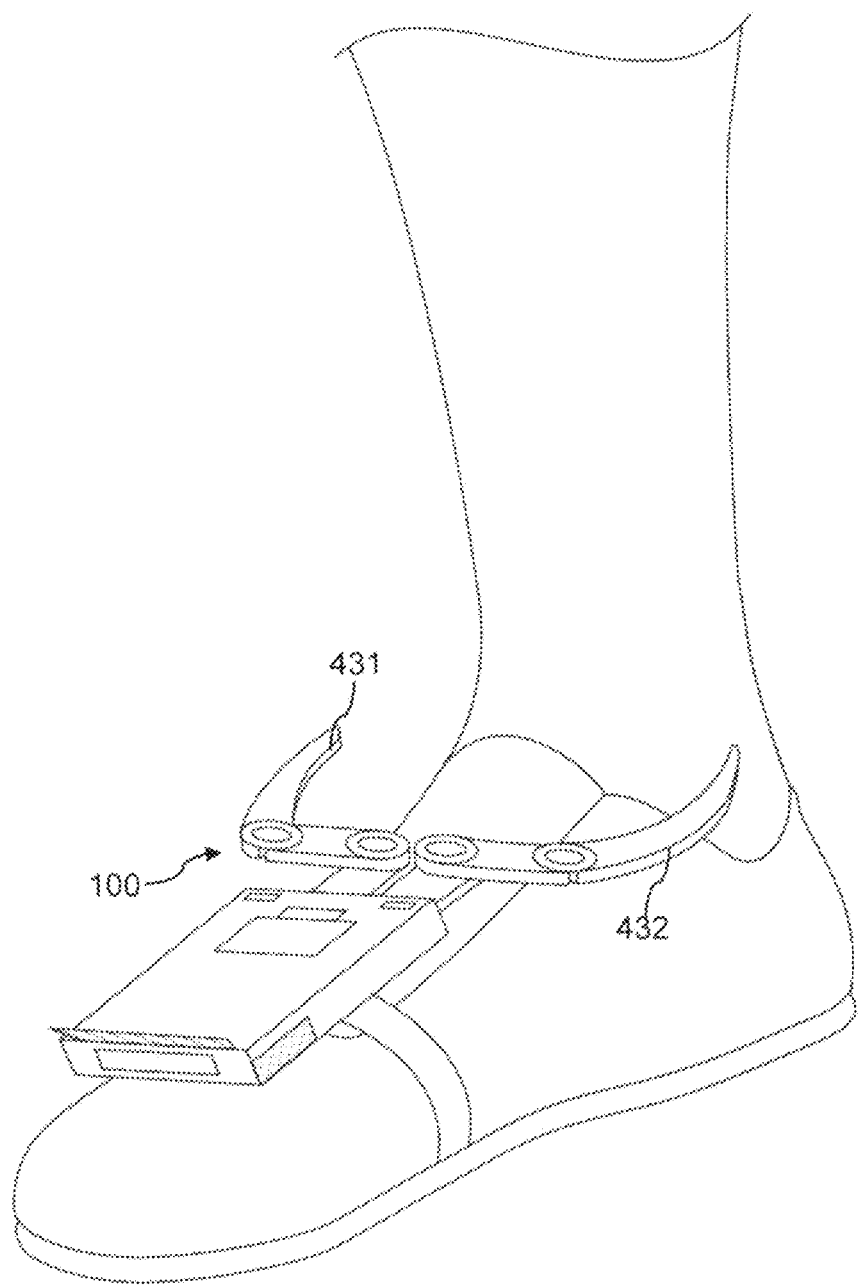
FIG. 4 is a schematic illustration of a wearable assistive device for the visually impaired according to another embodiment.

FIG. 4 shows an embodiment with a variation of the robotic arms 431, 432. For example, each of the robotic arms 431, 432 can be multi-joint arms, which may have a shape so as to surround a particular body part, such as a user's ankle. The joints may be individually controllable. For example, the joints may be individually controllable to give the user an indicator of an orientation or a position of a detected object relative to the user or a suggested direction of movement for the user based on the detected object.

The wearable assistive device 100, turned on with the switch 114 and fastened to a shoe, sandal or any appropriate footwear of a visually impaired user using the fastener 119, can help to increase or support the mobility of the user, by detecting an object within a predetermined distance in front of the wearable assistive device 100 and the user with the ultrasonic sensor 111. When such an object is detected by the ultrasonic sensor 111, for example, when the user is walking or running, the user is informed of the presence of the object when the robotic arms 131, 132 grip his or her ankle. In one or more embodiments, the gripping can be accompanied by an auditory signal and/or an auditory message emitted by the speakers 116, 117 and/or vibrations emitted by the vibrators 133, 134. In one or more embodiments, the GPS tracker 112 can be activated to determine a precise, real-time location of the user, record the position of the user at regular intervals and provide auditory and/or tactile directions or navigations to the user. The auditory and/or commands from the GPS can be communicated to the user via the speakers 117, 118 and the robotic arms 131, 132. The information display screen 115 can display GPS information and the status of the ultrasonic sensor 111 (e.g. "New object detected", "Scanning for a new object," etc.) whereas the time display screen 116 can indicate the current time and an estimated time distance between the user and the detected object, for example, based on the user's rate of movement, rate of acceleration, estimated likely course of action based on historical data (e.g. GPS data from a previous route traversed by the user of the device).

In one or more embodiments, the ultrasonic sensor 111 can be configured to determine one or more characteristics of a detected object. Such characteristics can include size, shape, dimensions, color and/or orientation. Using an external or a built-in processor (discussed in detail with respect to other embodiments but applicable here as well), the wearable assistive device 100 can identify or recognize the object and identification information can be communicated to the user by the robotic arms 131, 132 gripping his or her ankle in an object-specific manner or pattern. For example, when the presence of a car or a staircase is detected within the predetermined distance, the robotic arms can grip the user's ankles twice consecutively for 3 seconds each time with 3-second intervals in between. Alternatively, the robotic arms may be configured to grip the user's ankles for a prolonged period when a potentially dangerous object is detected. The robotic arms release the grip when the user moves away from the object. In one or more embodiments, the gripping can be accompanied by an object-specific auditory signal (e.g. Loud beeping with increasing frequency as the identified object gets closer) and/or an auditory message emitted by the speakers 116, 117 (e.g. "A staircase is detected at approximately 10 footsteps ahead of you") and object-specific vibrations emitted by the vibrators 133, 134 (e.g. vibrations with increasing frequency and strength as the identified object gets closer).

In certain embodiments, whenever touch alert and alarm signals have been activated, light emitter 113 may be activated concurrently to illuminate a detected object. This can be useful for a user who is not completely blind, the light helping the user to see the detected object better, so that the user can take appropriate action, such as stopping or going around the detected object.

In certain embodiments, the main arm 135, under the coordination of a motor or an actuator, can be movable, for example, to raise or lower the robotic arms 131, 132 to grip different portions of a user's leg other than the ankle.

In one or more embodiments, the mechanical component 130 and the electronic component 110 of wearable assistive device 100 may be detachable. To assemble the device, main arm 135 can connected to the electronic component 110. This embodiment may be appropriate when the mechanical and electronic components are acquired separately. Main arm 135 may emanate from a second side surface 102 which is opposite to the first side surface 101.

In an alternative embodiment, the mechanical and electronic components of wearable assistive device 100 may be one-piece.

Figure 5:
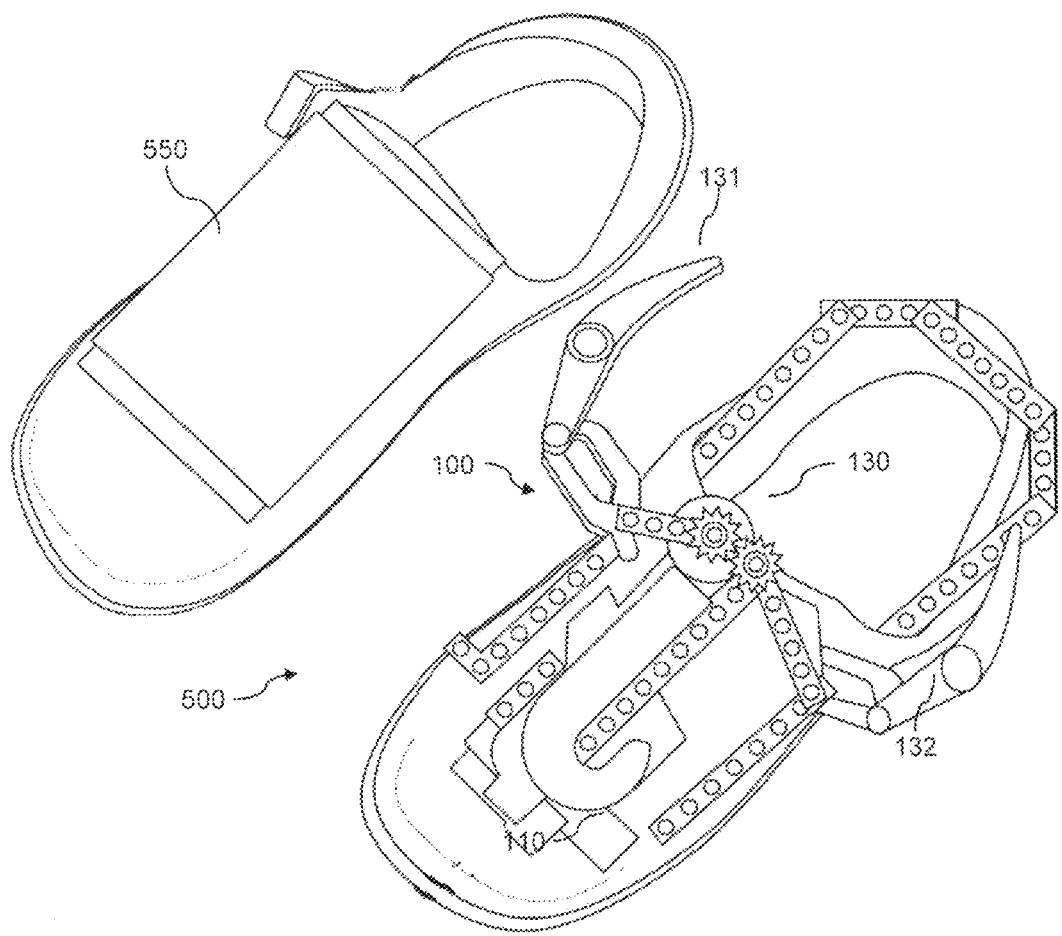
FIG. 5 is a schematic illustration of a wearable assistive system for the visually impaired according to yet another embodiment.

FIG. 5 illustrates the incorporation of wearable assistive device into wearable assistive system 500. In system 500, controller 550 can be a wearable computing device that performs multiple tasks, such as processing input signals from ultrasonic sensor 111 and GPS tracker 112, responding to the input signals through calculated and controlled output from robotic arms 131, 132, vibrators 133, 134, speakers 117, 118, information and time display screens 115, 116 and light emitter 113. Furthermore, controller 550 can include a timer mechanism that keeps time and measures time intervals for timing and coordination of signals. It will be readily understood by an ordinary skilled artisan that multiple software programs and algorithms would be required to perform all the various tasks of controller 550. Controller 550 can be electrically connected to electronic component 110 and mechanical component 130 of the wearable assistive device wirelessly or wired. Controller 550 can be attached securely to the user's other shoe through a fastener (not shown) similar to fastener 119 of wearable assistive device 100. Examples of the fasteners include plastic or metal clips, buttons, elastic straps, hook and loop connectors, buckles, strings etc.

In an alternative embodiment, controller 550 can be a built-in controller inside the wearable assistive device 100, and the wearable assistive system 500 may be one-piece.

Figure 6:
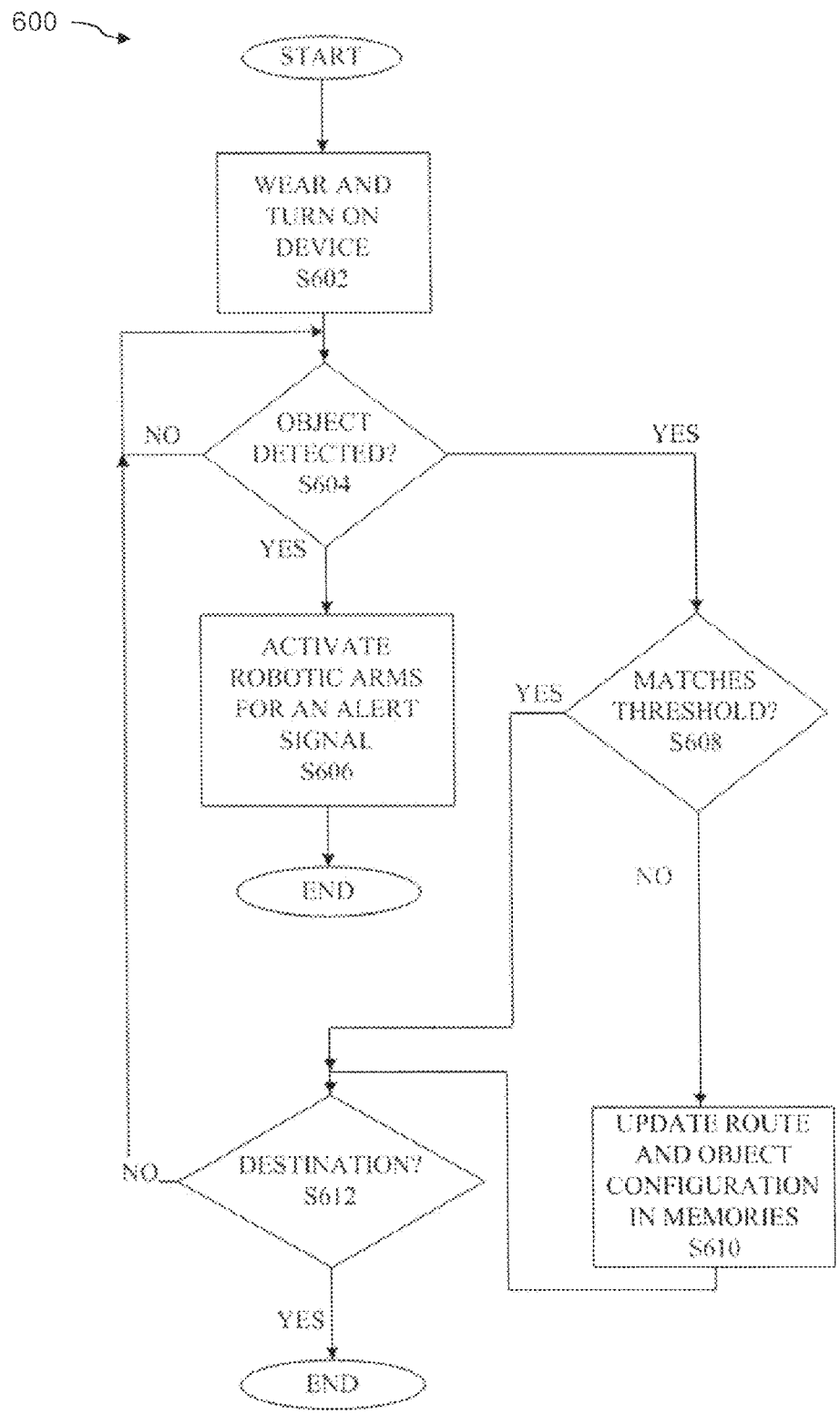
FIG. 6 is a flowchart illustrating a process or method according to one or more embodiments of the present invention.

FIG. 6 is a flowchart of a process 600 according to one or more embodiments. Generally, the process 600 can include detecting an object, activating an alarm and updating route information in a memory, using a wearable assistive system or device according to one or more embodiments. The process 600 can begin at step S602 where the user applies (attaches/secures) a wearable assistive device. The user can optionally choose a desired address to a destination, and activate the device with a switch. The destination may be a park, grocery store, workplace or restaurant that the user visits frequently, or a place that he or she is visiting for the first time. Once the device has been activated, the process 600 can proceed to step S604 where the device begins detecting stationary or moving objects in front of the user along a predetermined distance using the ultrasonic sensor 111 a route provided by GPS tracker 112, for instance. Of course, the device may also detect objects to each side of the user and/or behind the user. The predetermined distance may be preprogrammed in controller 550. In one embodiment, the predetermined distance may be 3 meters. In another embodiment, the predetermined distance may be 2 meters. In yet another embodiment, the predetermined distance may be 1 meter.

If no object is detected, the ultrasonic sensor 111 in wearable assistive device 100 can continue to check for an object within the predetermined distance at step S604.

However, if an object is detected by ultrasonic sensor 111, then process 600 can continue to both steps S606 and S608. At step S606, robotic arms 131, 132 can be activated to grip or contact the ankles of the user, for instance, for a predetermined amount of time, for example, 3 seconds, and/or in a predetermined pattern, as a signal to alert the user of the presence of an object within the predetermined distance. This touch alert signal may be accompanied by an auditory alert signal emitted by wearable assistive device 100 through speakers 117, 118. In certain embodiments, the frequency of the auditory alert signal may increase as the ultrasonic sensor 111 indicates that the detected object is getting closer. Similarly, the strength of the grip may increase as the user gets closer to the object. Conversely, the strength of the grip may decrease as the user moves further away. At the same time, at step S608, the size and/or shape of the detected object can be determined by ultrasonic sensor 111 and can be compared to a predetermined threshold size value that has been preprogrammed in controller 550. A database of geometrical shapes of different sizes that correlate with different objects found at destinations frequently visited by the user can be stored in a memory associated with the controller. For example, a park visited weekly by the user may be identified by a bench with rectangle dimensions of 150 cm×60 cm×100 cm (length×width×height) or a trash can with cylinder dimensions of 30 cm×120 cm (radius×height). The robotic arms 131, 132 or 431, 432 can be activated in a predetermined pattern, and/or for a predetermined amount of time to indicate to the user the particular object identified, object type or class. An auditory message may additionally or alternatively be provided to identify the particular object type or object class.

At step S608, if the size and/or shape of the detected object does not match a predetermined threshold value, then process 600 can proceed to step S612 in which a continuous, real-time verification of current location by the GPS tracker can be performed. If the current location does not match the desired address, process 600 can return to step S604. However, if the current location does match the desired address, then process 600 can proceed to step S614 where the device may be deactivated. Furthermore, if at step S608, the size and/or shape of the detected object does not match predetermined threshold value, then process 600 can proceed to step S610 where the route can be updated in the memory of GPS tracker and the dimensions of the detected object is updated and saved in a memory associated with controller 550.

Therefore, as described above, a user may use the wearable assistive system to assist them in reaching the same destination multiple times or a new destination. The wearable assistive system can identify a destination in one or more of the following ways. With a repeated destination that a user has visited, the destination can be identified with the satellite location by the GPS tracker, and objects associated with the location that are detected by the ultrasonic sensor and the dimensions of the object can be interpreted by the controller. New objects associated with the repeated destination may be detected and their dimensions can be updated and saved in the memory of the controller. For example, a user can go to the lakeside for his or her daily walk. The GPS tracker in the wearable assistive system can guide the user to the lakeside, and optionally the ultrasonic sensor 111. When the user reaches the lakeside, the wearable assistive system can identify and confirm that by GPS and at least one object found at the lakeside that the user encounters during his or her daily walk, for example, a trash can, bench, tree, rock, etc. If a new object is detected, for example, when the user takes a different route to the lakeside or visits a new destination, the new route and new object can be recorded and saved in memories associated with the GPS tracker and the controller, respectively.

Figure 7:
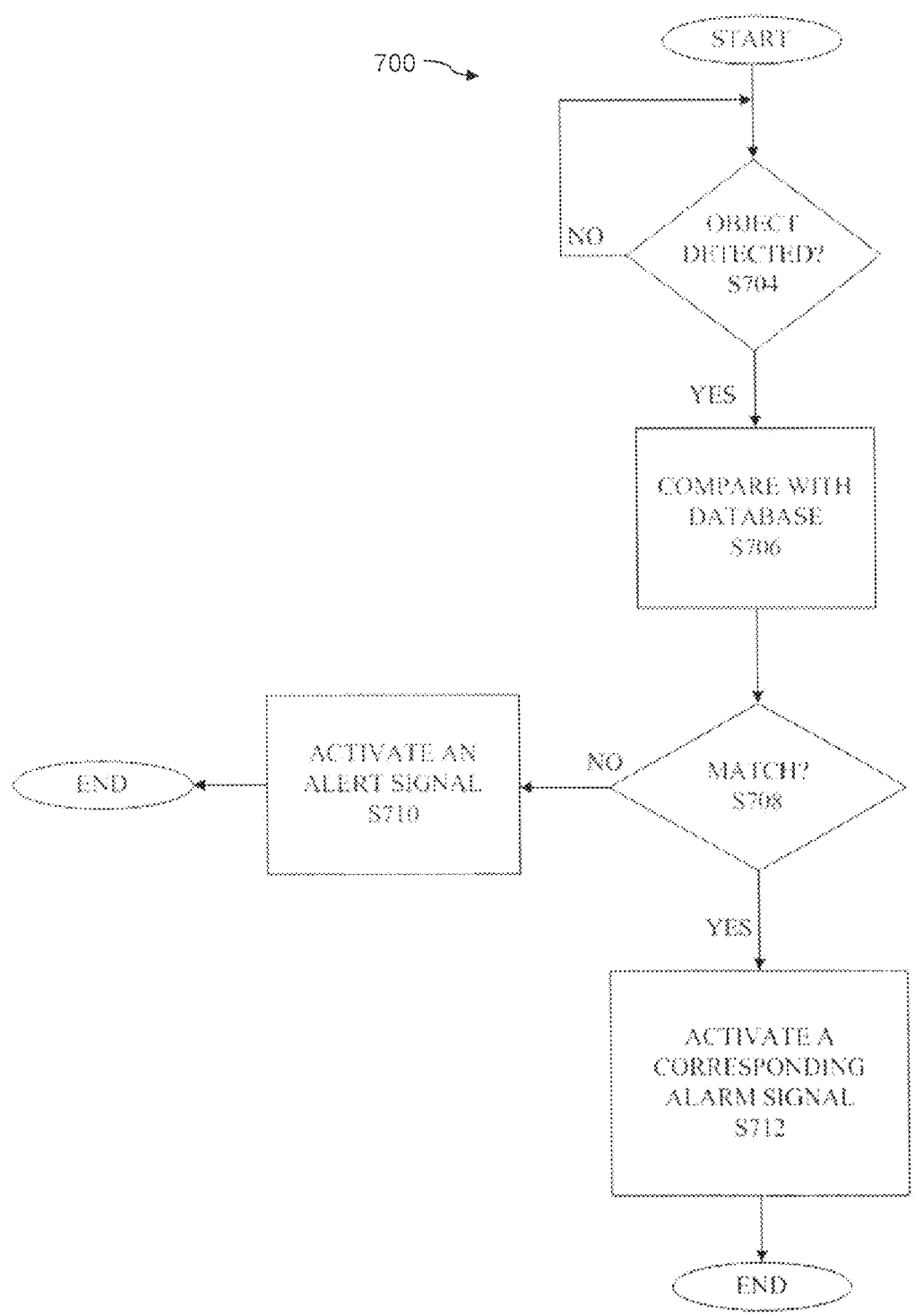
FIG. 7 is a flowchart illustrating a process or method according to another embodiment of the present invention.

In another embodiment, the present disclosure relates to a process of activating an object-specific alarm signal. The flowchart in FIG. 7 illustrates the process of activating an object-specific alarm signal, such as by wearable assistive system 500.

Process 700 can begin at step S704 where ultrasonic sensor 111 is activated and can detect objects in front of a user within a predetermined distance along a route provided by GPS tracker 112. Of course, like before, the ultrasonic sensor 111 can sense one or more sides of the user and/or behind the user. Examples of ranges for the predetermined distance have been previously described. If no object is detected within the predetermined distance, ultrasonic sensor 111 can continue to check for an object within the predetermined distance at step S704. However, if an object is detected, then process 700 can proceed to step S706 where the characteristics of the object (e.g. dimensions, color, orientation, etc.) detected by the ultrasonic sensor are compared to a database containing geometrical shape dimensions mapped upon multiple predetermined objects. This database can be saved in a memory associated with controller 550. At step S706, controller 550 can check if the characteristics of the detected object match the characteristics of any of the predetermined objects saved in the database.

If there is a match between characteristics of the detected object and the characteristics of a predetermined object recorded in the database, process 700 can proceed to step S712 wherein robotic arms 131, 132 can be activated to grip or contact the user's ankles and/or vibrate against the user's ankles as an alarm signal that an identified object is within the predetermined distance. With the use of one or more software algorithms to program the controller (implemented in computer hardware, computer software, circuitry, or a combination of two or more of the foregoing), the robotic arms may be configured to emit unique object-specific signals that correspond to different objects. For example, when the presence of a car or a staircase is detected within the predetermined distance, the robotic arms grip the user's ankles three times consecutively for 2 seconds each time with 2-second intervals in between. Alternatively, the robotic arms may be configured to grip the user's ankles for a prolonged period and/or with increased strength when a potentially dangerous object is detected. The robotic arms can release or reduce the grip when the user moves away from the object. The touch object-specific alarm signals may be simultaneously accompanied by object-specific, auditory alarm signals emitted through the speakers of wearable assistive device 100.

On the other hand, if the detected object does not match any of the predetermined objects in the database, process 700 can proceed to step S708 instead wherein a touch alert signal and optionally an equivalent auditory alert signal (identical to the alert signal at step S606) are activated.

Figure 8:
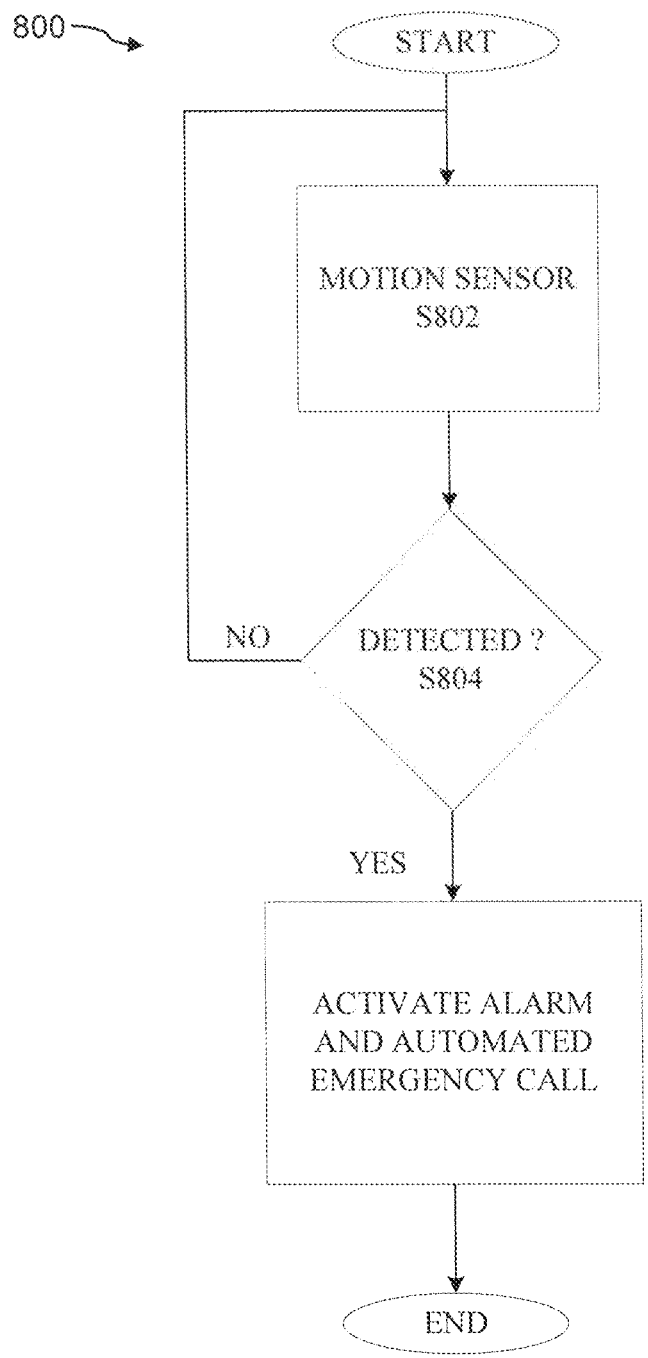
FIG. 8 is a flowchart illustrating a safety communication process or method according to one or more embodiments.

In yet another embodiment, wearable assistive system 500 can be equipped with an efficient emergency response. FIG. 8 is a flowchart illustrating the process of safety communication in an exemplary emergency situation.

Process 800 can begin at step S802, wherein a motion sensor is in an activated mode. The motion sensor may be ultrasonic sensor 111 or a separate device in wearable assistive device 100. At step S404, the motion sensor can check for a sudden motion (e.g. using a gyroscope or accelerometer internal or external to the wearable assistive device 100). If no sudden motion is detected, the motion sensor continues checking. However, if a sudden motion, for example, a fall or collision is detected by the motion sensor, process 800 can proceed to step S806, wherein an electric signal is sent to controller 550. An auditory emergency alarm signal can then be emitted through speakers 117, 118, for example, so that individuals around the user may be alerted and extend help to the user. At the same time, controller 550 can equipped with at least one wireless communication interface such as Bluetooth and Wifi via a transponder. During an emergency situation wherein a sudden motion has been detected, the controller 550 can connect to a mobile communication device that is integrated with the same wireless communication interface(s) as well as cellular technology. A software program or application of the mobile communication device can handle contacting a pre-assigned emergency personal contact or emergency medical services over a cellular network or Wifi. As wearable assistive device 100 can be GPS-integrated, the location of the user can also be communicated in the emergency call.

In any or all disclosed embodiments, any touch alert or object-specific alarm signal may be accompanied by tactile vibrations, auditory signals, auditory messages, light and combinations thereof, each of which can accurately reflect when one or more robotic arms is moved to squeeze the user's ankle. As touch or somatic sensation may be the primary sensory modality employed in one or more embodiments, the use of the wearable assistive device and system of the present disclosure is not confined to the visually impaired. For example, the device and the system may be used by people with hearing impairment for mobility assistance.

Figure 9:
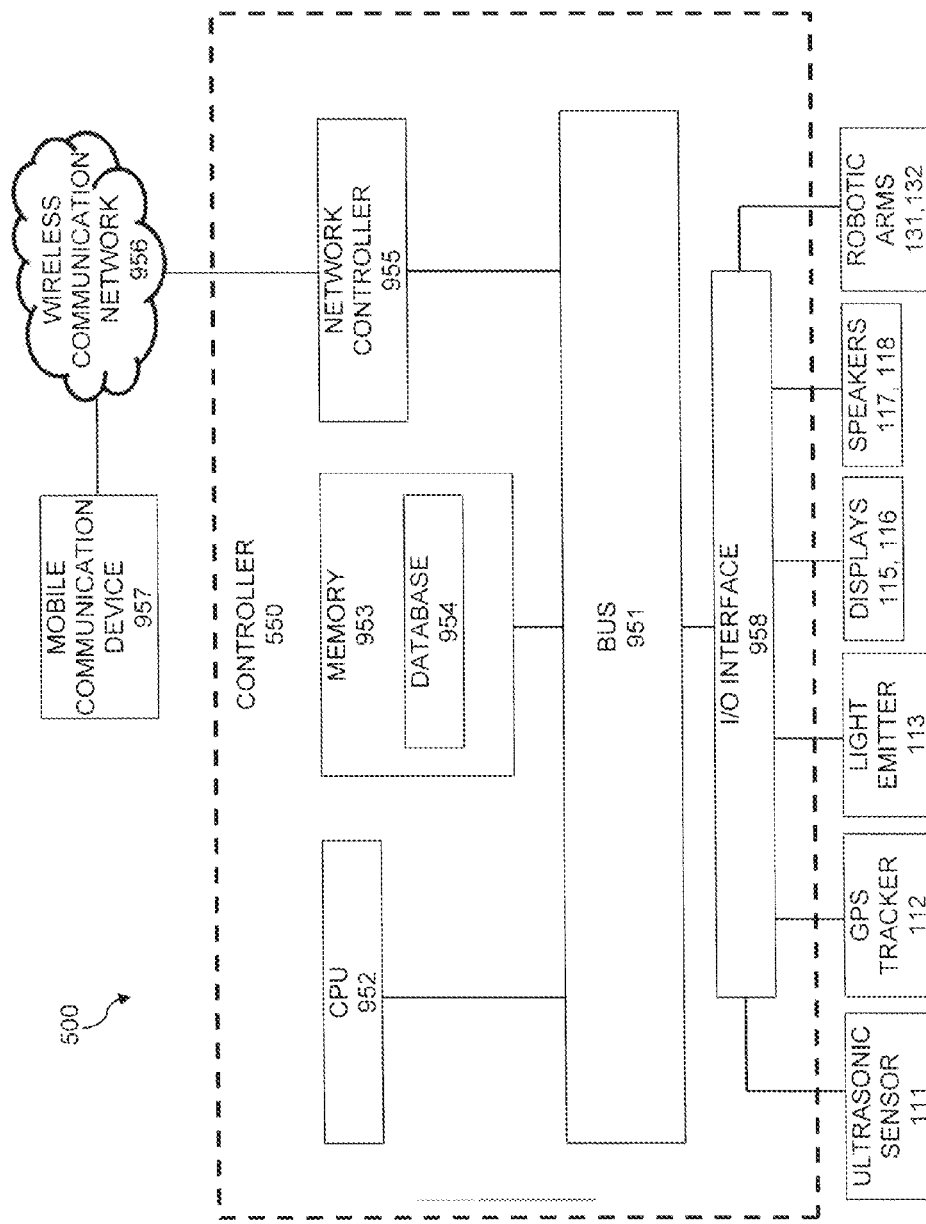
FIG. 9 is a block diagram of a computer system according to one or more embodiments.

FIG. 9 is a block diagram of the electronic components of wearable assistive system 500 according to an exemplary embodiment of the present disclosure. Controller 550 of system 500 can include a central processing unit (CPU) 952 which performs some or all processes that have been previously described. The process data and instructions may be stored in memory 953. These processes and instructions may also be stored on a storage medium disk such as a hard drive (HDD) or portable storage medium or may be stored remotely. Furthermore, databases of geometrical shape dimensions mapped upon multiple predetermined objects and GPS routes, maps and locations can be stored in memory 953. Embodiments are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the processing circuitry communicates, such as a server or computer.

Each of the electronic components may be implemented using software, hardware, circuitry, or a combination thereof. For example, controller 550 of wearable assistive 100 may be a hardware processor implemented in circuitry.

Further, the claimed advancements may be provided with or as a utility application, background daemon, or component of an operating system, or combination thereof, executing in conjunction with CPU 952 and an operating system such as Microsoft Windows 7, Microsoft Windows 8, UNIX, Solaris, LINUX, Apple MAC-OS and other systems known to those skilled in the art.

CPU 952 may be a Xenon or Core processor from Intel of America or an Opteron processor from AMD of America, or may be other processor types that would be recognized by one of ordinary skill in the art. Alternatively, the CPU 952 may be implemented on an FPGA, ASIC, PLD or using discrete logic circuits, as one of ordinary skill in the art would recognize. Further, CPU 952 may be implemented as multiple processors cooperatively working in parallel to perform the instructions of the inventive processes described above.

Controller 550 as shown in FIG. 9 can also include a network controller 955 (e.g. Bluetooth and/or Wifi) for interfacing with network 956. Network 956 can be a Bluetooth and/or Wifi wireless communication network or any other wireless communication network that may be available, that connects controller 550 to a mobile communication device 957 that is integrated with the same wireless communication interface(s) as well as cellular technology.

Controller 550 can also further include a general purpose input/output (I/O) interface 958. As can be seen in FIG. 9, all components within controller 550, namely the I/O interface 958, CPU 952, main memory 953, network controller 955, are connected to communication bus 951.

Peripherals such as ultrasonic sensor 111, GPS tracker 112, light emitter 113, displays (i.e. information and time display screens 115, 116), speakers 117, 118 and robotic arms 131, 132 can be connected to controller 550 via the I/O interface 958.

Thus, the foregoing discussion discloses and describes merely exemplary embodiments of the present invention. As will be understood by those skilled in the art, the present invention may be embodied in other specific forms without departing from the spirit or essential characteristics thereof.

Accordingly, the disclosure of the present invention is intended to be illustrative, but not limiting of the scope of the invention, the disclosure, or the claims.

The invention claimed is:

1. A hands-free, wearable assistive device configured to be worn on a portion of a leg of a user, comprising:
   an ultrasonic sensor configured to detect an object within a predetermined distance in front of the device and the user;
   a processing circuitry configured to determine a plurality of characteristics of the object and identify the object based on detection signals from the ultrasonic sensor, and to determine when the object is within the predetermined distance;
   a GPS tracker circuitry configured to determine a real-time location of the user and to provide commands to output audible and/or tactile directions to a desired destination; and
   first and second robotic arms configured to grip the portion of the user's leg when the processing circuitry determines the object is within the predetermined distance in front of the device and based on the commands from the GPS tracker circuitry.

2. The wearable assistive device of claim 1, wherein the characteristics of the object comprise one or more dimensions, color and orientation of the object.

3. The wearable assistive device of claim 1, further comprising a motion sensor.

4. The wearable assistive device of claim 1, wherein the ultrasonic sensor is further configured to detect motion.

5. The wearable assistive device of claim 1, further comprising a light emitter.

6. The wearable assistive device of claim 1, further comprising one or more speakers, each of which is configured:
   to emit auditory signals and/or messages when the ultrasonic sensor detects the object; and
   to emit object-specific auditory signals and/or messages when the processing circuitry determines the characteristics of the object and identifies the object.

7. The wearable assistive device of claim 1, further comprising first and second vibrators on the first and the second robotic arms respectively, each of which is configured:
   to emit vibrations when the ultrasonic sensor detects the object; and
   to emit object-specific vibrations when the processing circuitry determines the characteristics of the object and identifies the object.

8. A wearable assistive system configured to be worn on a portion of one or more legs of a user, comprising:
   a device including:
      an ultrasonic sensor configured to detect an object within a predetermined distance in front of the device and the user, to determine the characteristics of the object and to identify the object,
      a GPS tracker configured to determine a real-time satellite location of a user and to provide audible and/or tactile directions to a desired destination, and
      first and second robotic arms configured to grip the user's ankle when the ultrasonic sensor detects the object within the predetermined distance in front of the device and the user and grip the user's ankle in an object-specific pattern when the ultrasonic sensor identifies the object; and
   a controller electrically connected to the device, including a processor, a memory and a database of geometrical shape dimensions mapped to multiple predetermined objects.

9. The wearable assistive system of claim 8, wherein the characteristics of the object comprise one or more dimensions, color and orientation of the object.

10. The wearable assistive system of claim 8, wherein the controller is a built-in controller inside the device.

11. The wearable assistive system of claim 8, further comprising a motion sensor.

12. The wearable assistive system of claim 8, wherein the ultrasonic sensor is further configured to detect motion.

13. The wearable assistive system of claim 8, further comprising a Bluetooth or a Wifi transponder that connects the wearable assistive system to a mobile communication device.

14. The wearable assistive system of claim 8, further comprising a light emitter.

15. The wearable assistive system of claim 8, further comprising one or more speakers, each of which is configured:
   to emit auditory signals when the ultrasonic sensor detects the object; and
   to emit object-specific auditory signals when the ultrasonic sensor determines the characteristics of the object and identifies the object.

16. The wearable assistive system of claim 8, further comprising first and second vibrators on the first and the second robotic arms, respectively, each of which is configured:
   to emit vibrations when the ultrasonic sensor detects the object; and
   to emit object-specific vibrations when the ultrasonic sensor determines the characteristics of the object and identifies the object.

17. A method of providing mobility assistance to a user, comprising:
   providing a hands-free, wearable assistive system configured to be worn on one or more ankles of the user;
   detecting an object using an ultrasonic sensor of the system;
   determining, using a processor, whether the object is within a predetermined distance;
   gripping the one or more ankles of the user, when the object is within the predetermined distance, using first and second robotic arms of the system; and
   providing, using a GPS tracker, audible and/or tactile indications of directions to a desired destination.

18. The method of claim 17, further comprising:
   determining one or more characteristics of the object and identifying the object using the ultrasonic sensor and the processor; and
   gripping the user's ankle in an object-specific pattern based on the determining.

19. The method of claim 17, further comprising:
   emitting auditory signals and/or messages when the ultrasonic sensor detects the object, using one or more speakers; and
   emitting object-specific auditory signals and/or messages when the ultrasonic sensor and the processor determine the one or more characteristics of the object and identify the object, using the one or more speakers.

20. The method of claim 17, further comprising:
   emitting vibrations when the ultrasonic sensor detects the object, using first and second vibrators on the robotic arms, respectively; and
   emitting object-specific vibrations when the ultrasonic sensor and the processor determine the one or more characteristics of the object and identify the object, using the first and second vibrators on the robotics.

* * * * *